US012682670B2

(12) United States Patent
Karmakar et al.

(10) Patent No.: US 12,682,670 B2
(45) Date of Patent: Jul. 14, 2026

(54) PREDICTIVE MODEL FOR MEDICAL SIGNATURES

(71) Applicant: Express Scripts Strategic Development, Inc., St. Louis, MO (US)

(72) Inventors: Buddhadeb Karmakar, Leander, TX (US); Murlidhar Loka, Breinigsville, PA (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 204 days.

(21) Appl. No.: 18/386,882

(22) Filed: Nov. 3, 2023

(65) Prior Publication Data

US 2025/0148818 A1 May 8, 2025

(51) Int. Cl.
| | |
|---|---|
| *G06V 30/12* | (2022.01) |
| *G06V 30/19* | (2022.01) |
| *G06V 30/196* | (2022.01) |
| *G06V 30/226* | (2022.01) |
| *G16H 20/10* | (2018.01) |

(52) U.S. Cl.
CPC ........ *G06V 30/127* (2022.01); *G06V 30/1916* (2022.01); *G06V 30/196* (2022.01); *G06V 30/226* (2022.01); *G16H 20/10* (2018.01)

(58) Field of Classification Search
None
See application file for complete search history.

(56) References Cited

U.S. PATENT DOCUMENTS

| | | | |
|---|---|---|---|
| 7,260,402 B1 | 8/2007 | Ahmed | |
| 9,852,261 B1 | 12/2017 | Havard | |
| 10,886,025 B2 | 1/2021 | Kosaka | |
| 10,957,434 B2 | 3/2021 | Kozloski | |
| 10,957,435 B2 | 3/2021 | Kumar | |
| 11,514,528 B1 * | 11/2022 | Ciliberti | G06F 18/214 |
| 2004/0162740 A1 | 8/2004 | Ericsson | |
| 2006/0217824 A1 | 9/2006 | Allmon | |
| 2006/0249423 A1 | 11/2006 | Reijonen | |
| 2006/0261145 A1 | 11/2006 | Robertson | |
| 2010/0063836 A1 | 3/2010 | Ballard | |
| 2010/0324936 A1 | 12/2010 | Venkata | |
| 2013/0151273 A1 | 6/2013 | Jones | |
| 2013/0262155 A1 | 10/2013 | Hinkamp | |
| 2014/0046696 A1 | 2/2014 | Higgins | |
| 2014/0257832 A1 | 9/2014 | Hermiz | |
| 2018/0365385 A1 | 12/2018 | Cooney | |
| 2019/0259482 A1 * | 8/2019 | Puirava | G06N 20/00 |
| 2023/0011684 A1 | 1/2023 | Dey | |
| 2024/0013881 A1 * | 1/2024 | Lytvynenko | H04L 9/321 |

* cited by examiner

*Primary Examiner* — Andrew H Lam

(74) *Attorney, Agent, or Firm* — Jordan IP Law PC

(57) ABSTRACT

Methods and systems for predicting medical signatures are provided. The methods and systems access a communication comprising a medicinal drug prescription associated with a patient, the medicinal drug prescription being provided in the communication by a healthcare professional. The methods and systems process, by a first machine learning model, the communication to extract a plurality of entities from the medicinal drug prescription and apply a second machine learning model to the plurality of entities to predict a medical signature. The predicted medical signature comprises directions for the patient to follow to take the medicinal drug. The methods and systems cause a label with the medical signature to be printed and applied to a container that includes the medicinal drug.

19 Claims, 9 Drawing Sheets

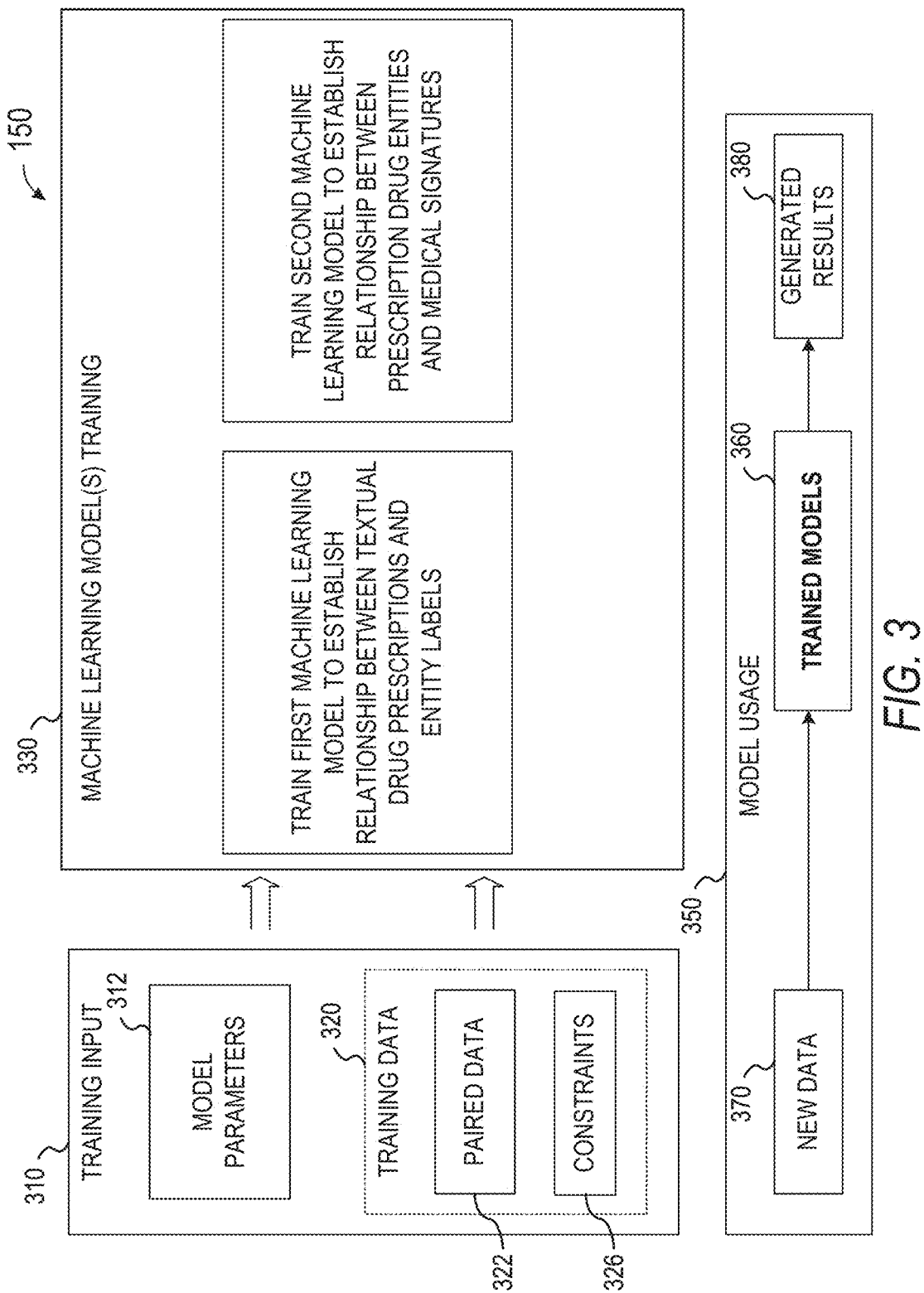

150

MACHINE LEARNING MODEL(S) TRAINING 330

TRAIN FIRST MACHINE LEARNING MODEL TO ESTABLISH RELATIONSHIP BETWEEN TEXTUAL DRUG PRESCRIPTIONS AND ENTITY LABELS

TRAIN SECOND MACHINE LEARNING MODEL TO ESTABLISH RELATIONSHIP BETWEEN PRESCRIPTION DRUG ENTITIES AND MEDICAL SIGNATURES

TRAINING INPUT 310

MODEL PARAMETERS 312

TRAINING DATA 320

PAIRED DATA 322

CONSTRAINTS 326

350

MODEL USAGE

NEW DATA 370

TRAINED MODELS 360

GENERATED RESULTS 380

*FIG. 3*

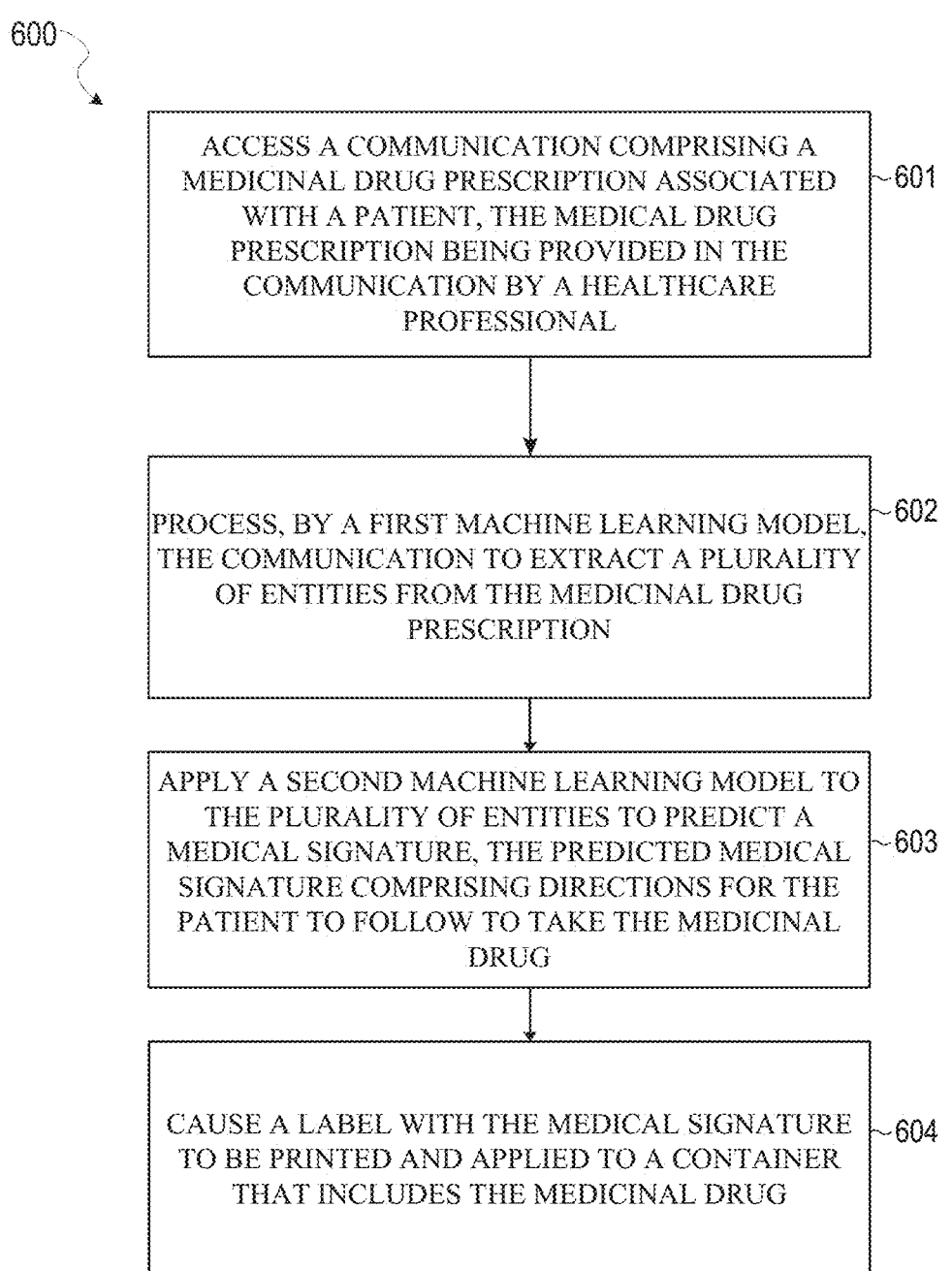

600

ACCESS A COMMUNICATION COMPRISING A
MEDICINAL DRUG PRESCRIPTION ASSOCIATED
WITH A PATIENT, THE MEDICAL DRUG
PRESCRIPTION BEING PROVIDED IN THE
COMMUNICATION BY A HEALTHCARE
PROFESSIONAL                                      ⎬601

PROCESS, BY A FIRST MACHINE LEARNING MODEL, ⎬602
THE COMMUNICATION TO EXTRACT A PLURALITY
OF ENTITIES FROM THE MEDICINAL DRUG
PRESCRIPTION

APPLY A SECOND MACHINE LEARNING MODEL TO
THE PLURALITY OF ENTITIES TO PREDICT A
MEDICAL SIGNATURE, THE PREDICTED MEDICAL  ⎬603
SIGNATURE COMPRISING DIRECTIONS FOR THE
PATIENT TO FOLLOW TO TAKE THE MEDICINAL
DRUG

CAUSE A LABEL WITH THE MEDICAL SIGNATURE ⎬604
TO BE PRINTED AND APPLIED TO A CONTAINER
THAT INCLUDES THE MEDICINAL DRUG

FIG. 6

API CALLS
708

MESSAGES
712

PREDICTIVE MODEL FOR MEDICAL SIGNATURES

BACKGROUND

Patient medical records are managed in a variety of ways. Certain medical records include prescriptions for medicinal drugs (also referred to as drug prescriptions) that are written or provided by various healthcare professionals. These prescriptions are usually processed by pharmacists to dispense the corresponding medications to a patient.

BRIEF DESCRIPTION OF THE DRAWINGS

FIG. 3 is a block diagram of an example patient management platform that may be deployed within the system of FIG. 1, according to some examples.

FIG. 6 is a flowchart illustrating example operations of the patient management platform, according to some examples.

DETAILED DESCRIPTION

Figure 1:
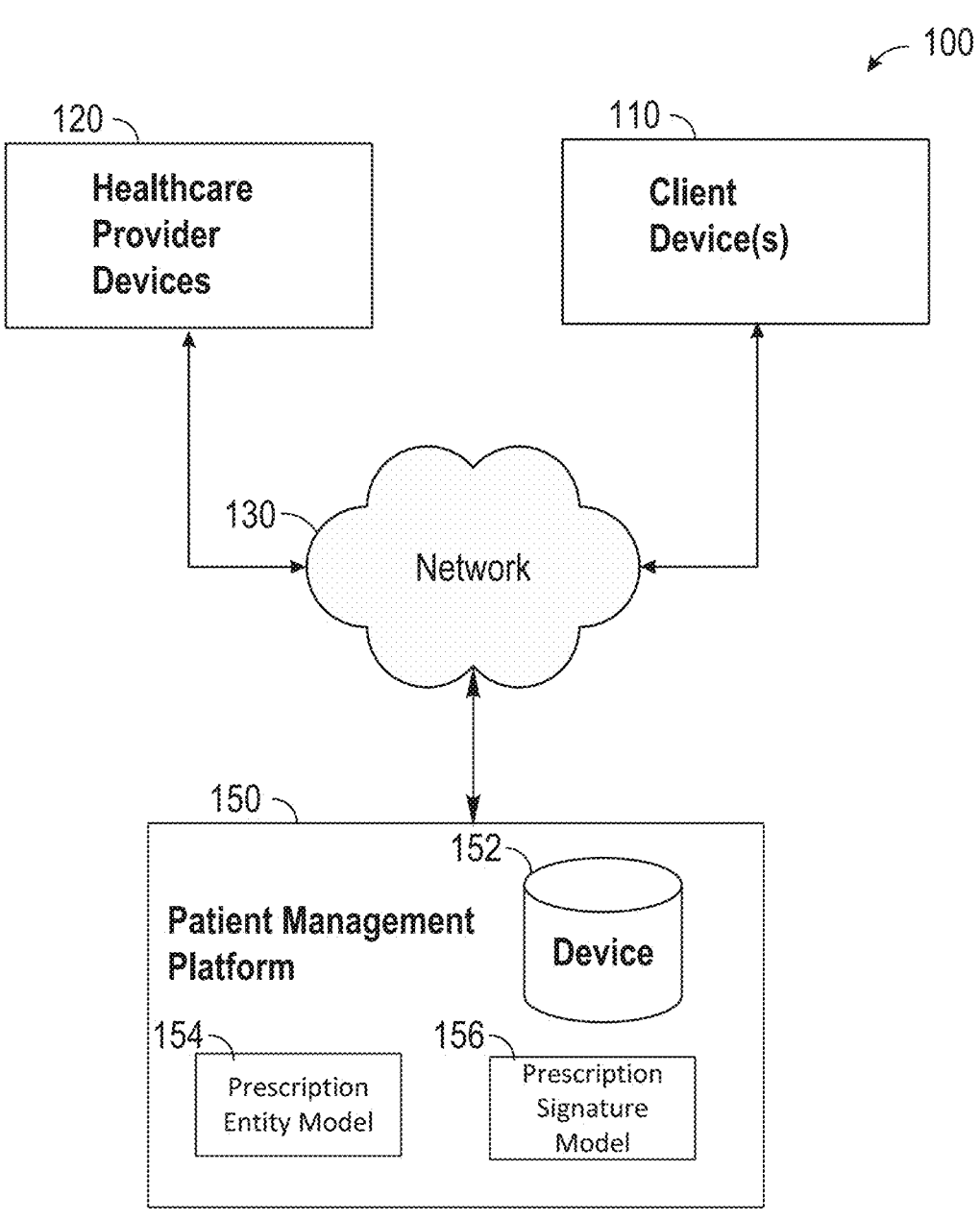
FIG. 1 is a block diagram of an example patient management platform, according to some examples.

Example methods and systems for a patient management platform are provided. Specifically, the methods and systems predict medical signatures (sig prediction) for medicinal drug prescriptions obtained from one or more healthcare professionals. The sig predictions, if approved by a pharmacist or other operator, can then be printed on a label that is attached to a container of the medicinal drugs for which the medicinal drug prescription was received. The container with the label attached can then be dispensed to a patient. In the following description, for purposes of explanation, numerous specific details are set forth in order to provide a thorough understanding of the examples. It will be evident, however, to one of ordinary skill in the art that examples of the disclosure may be practiced without these specific details.

A prescription, often abbreviated ℞ or Rx, is a formal communication from a physician or other registered healthcare professional to a pharmacist, authorizing them to dispense a specific prescription drug (also referred to as medicinal drug) for a specific patient. Usually, a doctor writes direction on how to take a particular medication in a direction field of the prescription. The direction written by doctor is most of time in short form and lacks any standardization. The direction can also contain various abbreviations which may or may not be understandable by patient. Pharmacist manually review the direction text in the prescription and manually standardize the direction text often with some correction before sending the standardized text to patients so that patients can follow the direction easily without any confusion. The communication from the pharmacist to the patient on the label for the prescription drugs is referred to as a medical signature (or sig text).

Medical signatures are normally written on the top of the medication (medicinal drug) bottle/package so that patient can follow the directions while taking the medication. The sig text provides a short, concise and appropriate direction for how the patient should take the medication and is usually derived from the prescription obtained from the healthcare professional (e.g., physician). Technicians and pharmacist spend considerable amount of time to write the sig text for each prescription manually. This can also introduce manual errors which can have disastrous consequences if followed by the patient improperly. As a result, users are burdened with having to navigate multiple pages of information to look up the appropriate way to write the sig text and repeatedly inputting information to generate sig text from prescriptions. This wastes a great deal of time and resources that can be devoted to other tasks.

The disclosed techniques provide systems and methods to automate sig text generation. The disclosed techniques access a communication (e.g., electronic, verbal, or hand-written) including a medicinal drug prescription associated with a patient. The medicinal drug prescription being provided in the communication by a healthcare professional. The disclosed techniques process, by a first machine learning model, the communication to extract a plurality of entities from the medicinal drug prescription and apply a second machine learning model to the plurality of entities to predict a medical signature. The predicted medical signature includes directions for the patient to follow to take the medicinal drug. The disclosed techniques cause a label with the medical signature to be printed and applied to a container that includes the medicinal drug.

As a result, a great deal of time and resources are saved, and the user need not have to navigate through a multitude of pages of information to generate sig text. This saves time and reduces the amount of resources needed to accomplish a task.

FIG. 1 is a block diagram showing an example patient management system 100, according to some examples. The patient management system 100 includes one or more client devices 110, one or more healthcare provider devices 120, and a patient management platform 150 that are communicatively coupled over a network 130 (e.g., Internet, telephony network).

As used herein, the term "client device" may refer to any machine that interfaces to a communications network (such as network 130) to access the patient management platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multiprocessor systems, microprocessor-based or programmable consumer electronics, game consoles, set-top boxes, or any other communication device that a user may use to access a network or the patient management platform 150.

In some cases, the patient management platform 150 is accessible over a global communication system, e.g., the Internet or world wide web. In such instances, the patient management platform 150 hosts a website that is accessible to the client devices 110. Upon accessing the website, the client devices 110 provide secure login credentials, which are used to access a profile associated with the login credentials and one or more patient profiles or patient information. As used herein, patient information includes any medical information associated with a patient including one or more medicinal drug prescriptions, prior medical insurance claims that were approved or denied, one or more electronic health records or medical health records, patient health information, patient demographic information, prior bloodwork results, prior results of non-bloodwork tests, medical history, medical provider notes in the electronic health record, intake forms completed by the patient, patient in-network insurance coverage, patient out-of-network insurance coverage, patient location, and/or one or more treatment preferences. One or more user interfaces associated with the patient management platform 150 are provided over the Internet via the website to the client devices 110. The user interfaces may include set locations or fixed locations whereat it displays the patient data.

Healthcare provider devices 120 can include the same or similar functionality as client devices 110 for accessing the patient management platform 150. In some cases, the healthcare provider devices 120 are used by "internal" users. Internal users are medical professionals, such as medical personnel, physicians, healthcare professionals, clinicians, healthcare providers, health-related coaches pharmacy benefit manager (PBM) operators, pharmacists, specialty pharmacy operators or pharmacists, or the like that are associated with, certified by, or employed by one or more organizations that provides the patient management platform 150. In some cases, the healthcare provider devices 120 are used by "external" users.

The healthcare provider devices 120 are used to access the patient management platform 150 and view many records associated with many different patients (or users associated with client devices 110) and their respective patient information. Different levels of authorization can be associated with different users to control which records the users have access. In some instances, only records associated with those patients to which a given user is referred, are made accessible and available to the given user device. Sometimes, a first user can refer a patient or records associated with the patient to a second user. In such circumstances, the second user becomes automatically authorized to access and view the patient's records that were referred by the first user. The user interfaces on the healthcare provider devices 120 may include set locations or fixed locations whereat it displays the patient data.

In some examples, the patient management platform 150 (and specifically the prescription entity model 154 and prescription signature model 156) can implement one or more machine learning models, such as one or more neural networks (discussed below in connection with FIGS. 3 and 9). The patient management platform 150 can use the machine learning models to simplify and expedite the management of patient information and particularly to generate or predict medical signatures from medicinal drug prescriptions that are obtained from healthcare professionals. Particularly, the patient management platform 150 can be accessed by the healthcare provider devices 120. A first one of the healthcare provider devices 120 of a healthcare professional can be used to navigate to a prescription page to write a prescription for a medicinal drug for a patient. The written prescription can then be delivered to or communicated to a second one of the healthcare provider devices 120. In some cases, the written prescription can be communicated to the second one of the healthcare provider devices 120 through one or more channels, such as a voice channel (where the written prescription is spoken verbally to a pharmacist associated with the second one of the healthcare provider devices 120); a facsimile (fax) transmission channel; an electronic prescription drug transmission channel, or a physical medium, such as hand delivery of a paper or document containing the prescription. The second one of the healthcare provider devices 120 can generate a document with text containing the prescription received from the first one of the healthcare provider devices 120.

To improve the accuracy and efficiency at which a medical signature is generated from the prescription that is received, the patient management platform 150 can process or analyze the prescription using a first machine learning model (e.g., the prescription entity model 154) to extract one or more entities from the prescription. The one or more entities can then be processed or analyzed by a second machine learning model (e.g., the prescription signature model 156) to generate or predict the medical signature. The patient management platform 150 can validate the predicted medical signature and generate a confidence score associated with the prediction. The patient management platform 150 can present a GUI to the pharmacist, such as on the second one of the healthcare provider devices 120. The GUI can include the prescription received from the first one of the healthcare provider devices 120, the predicted medical signature, the confidence level associated with the predicted medical signature, and/or whether the predicted medical signature has passed the validation. In response, the patient management platform 150 can receive input from the second one of the healthcare provider devices 120 indicating whether the predicted medical signature is approved or accepted. In such cases, the generates instructions for a dispensing engine to print a label that contains the predicted medical signature and attach the label to a container of the medicinal drug of the prescription. In response to receiving input that modifies the predicted medical signature, the patient management platform 150 updates training data with the adjusted predicted medical signature. The patient management platform 150 can re-train the prescription signature model 156 using the adjusted predicted medical signature as the ground truth medical signature for the entities generated by the prescription entity model 154 for the prescription received from the first one of the healthcare provider devices 120.

In some aspects, the patient management platform 150 generates a confidence score for the medical signature. The confidence score and the predicted medical signature can be presented to a pharmacist for evaluation prior to printing the label. In some examples, the patient management platform 150 determines that the confidence score fails to transgress a threshold. In such cases, the patient management platform 150 triggers an alert for a pharmacist or other healthcare professional to review the predicted medical signature.

In some examples, the patient management platform 150 pre-processes the medicinal drug prescription (obtained from the healthcare professional) to optimize text including the medicinal drug prescription. The patient management platform 150, after optimizing the text, processes the optimized text as part of the document to extract the plurality of entities. For example, the patient management platform 150 can pre-processes the medicinal drug prescription by performing any one or combination of the following operations: removing extra spaces from the medicinal drug prescription, correcting spelling in the medicinal drug prescription, replacing medical abbreviations in the medicinal drug prescription, replacing common abbreviations in the medicinal drug prescription, formatting a national drug code (NDC) in the medicinal drug prescription, converting words to numbers in the medicinal drug prescription, removing number separators in the medicinal drug prescription, inserting a single space between a number and a word in the medicinal drug prescription, formatting medical number patterns in the medicinal drug prescription, replacing synonyms in the medicinal drug prescription with predetermined words, correcting concatenated words in the medicinal drug prescription, formatting special characters in the medicinal drug prescription, or correcting plural forms of words in the medicinal drug prescription.

In some examples, the medicinal drug prescription can be accessed by the patient management platform 150 from one of a plurality of channels including a fax transmission channel, electronic prescription transmission channel, and voice transmission channel. In some cases, the patient management platform 150 processes the predicted medical signature by a validation engine to determine whether the predicted medical signature is compliant according to dispensing practice guidelines (DPG). The DPG guidelines specify a manner in which medical signature text is written for different types of prescription drugs.

In some examples, the patient management platform 150 trains the prescription entity model 154 by performing training operations including obtaining a batch of training data including a first collection of textual drug prescriptions associated with a first set of ground truth entity labels for different components of the first collection of textual drug prescriptions. The prescription entity model 154 processes the first collection of textual drug prescriptions to generate an estimated set of entity labels and computes a loss based on a deviation between the estimated set of entity labels and the first set of ground truth entity labels. The prescription entity model 154 updating one or more parameters of the prescription entity model 154 based on the computed loss. The patient management platform 150 repeats these training operations for multiple batches of the training data and completes training of the prescription entity model 154 when a stopping condition/criterion is reached.

In some aspects, the patient management platform 150 trains the prescription signature model 156 by performing training operations including obtaining a batch of training data including a first collection of prescription drug entities corresponding to prescriptions received from one or more healthcare professionals associated with a first set of ground truth medical signatures generated by one or more pharmacists for the prescriptions. The prescription signature model 156 processes the first collection of prescription drug entities to generate an estimated set of medical signature predictions and computes a loss based on a deviation between the estimated set of medical signature predictions and the first set of ground truth medical signature predictions. The prescription signature model 156 updates one or more parameters of the prescription signature model 156 based on the computed loss. The patient management platform 150 repeats these training operations for multiple batches of the training data and completes training of the prescription signature model 156 when a stopping condition/criterion is reached.

In some examples, the patient management platform 150 computes similarity between the predicted medical signature and a known set of medical signatures. The similarity can include a cosine similarity. In some aspects, the patient management platform 150, in response to computing the similarity, determines that the predicted medical signature is missing one or more mandatory signature entities. The patient management platform 150 processes one or more of the known set of medical signatures using statistical probability to predict one or more values for the one or more mandatory signature entities that are missing from the predicted medical signature. The predicted medical signature can then be revised by the patient management platform 150 using the predicted one or more values.

In some examples, the plurality of entities generated by the prescription entity model 154 include any combination or all of the following entities: an action, a dose including an amount and unit, a strength including an amount and unit, a route, a frequency, a dose start time, a cycle including unit, duration and span, a dose duration, and/or additional healthcare professional instruction. The action entity can represent different actions written by a pharmacist, such as Take, Infuse, Chew, Inject, Apply etc. The route entity can represent where to take the medication like mouth, eye, under the skin, forehead, skin etc. The dose entity can represent or signify how much dose of the medication a patient should take like 1 tablet, 2 Injections. The dosage amount entity can represent the number before the dosage form like 2 in 2 tablets. The dosage form entity can represent one or more dosage forms, such as tablet, syringe, capsules etc. The strength entity can represent the amount of drug in a given dosage form, for example 500 MG. The strength amount entity can represent the number portion of the strength. The strength unit entity can represent the unit of the strength like MG. The frequency entity can represent what is the frequency of taking this medication by the patient like every day, weekly, twice in a day etc. The cycle entity can represent whether the medication needs to be taken in cycles. The on cycle span entity can represent the time span of the on period of a cycle. The on cycle duration entity can represent the duration of the on cycle. The on cycle unit entity can represent the unit of the on cycle, such as day, month, year, week etc. The off cycle span entity can represent the time span of the off period of the cycle. The off cycle duration entity can represent the duration of the off cycle. The off cycle unit entity can represent the unit of the off cycle, such as a day, month, year, week etc. The duration entity can represent the total duration of the medication. The specific dose time entity can represent at what specific time the medication needs to be taken by the patient, such as in morning, at 2:00 PM etc. The additional instruction entity can represent whether there are some additional instruction given by healthcare professional or based on drug which needs to be part of the sig text like "As directed by physician", "through unused portion" etc. The MD instruction entity can represent any specific instruction given by doctor is part of it. The drug specific instruction entity can represent whether the drug is of a certain class with specific instruction which needs to be mentioned in the sig text. The fractional numbers entity can represent whether fraction numbers need special treatment.

In some examples, the patient management platform 150 processes the medicinal drug prescription to detect a drug identifier. The patient management platform 150 can retrieve, from a database, values for a subset of the plurality of entities associated with the drug identifier. For example, the drug identifier, such as the national drug code (NDC) value and/or generic containment number (GCN), can help provide the required information to extract different drug entities like dosage form, strength, package size, and type etc. Drug entity can be used during prediction and also during application or verification of the DPG compliance rules.

The network 130 may include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The healthcare provider devices 120 can be used to access pharmacy claims, medical data (e.g., medical information 230 stored in database 152), laboratory data and the like for one or more patients that the healthcare provider devices 120 are authorized to view. This patient information 210 can be maintained in a database 152 by the patient management platform 150 or in a third-party database accessible to the patient management platform 150 and/or the healthcare provider devices 120.

In some examples, the client devices 110 and the patient management platform 150 can be communicatively coupled via an audio call (e.g., VoIP, Public Switched Telephone Network, cellular communication network, etc.) or via electronic messages (e.g., online chat, instant messaging, text messaging, email, and the like). While FIG. 1 illustrates a single client device 110 and a single healthcare provider device 120, it is understood that a plurality of such devices can be included in the system 100 in other embodiments.

Figure 2:
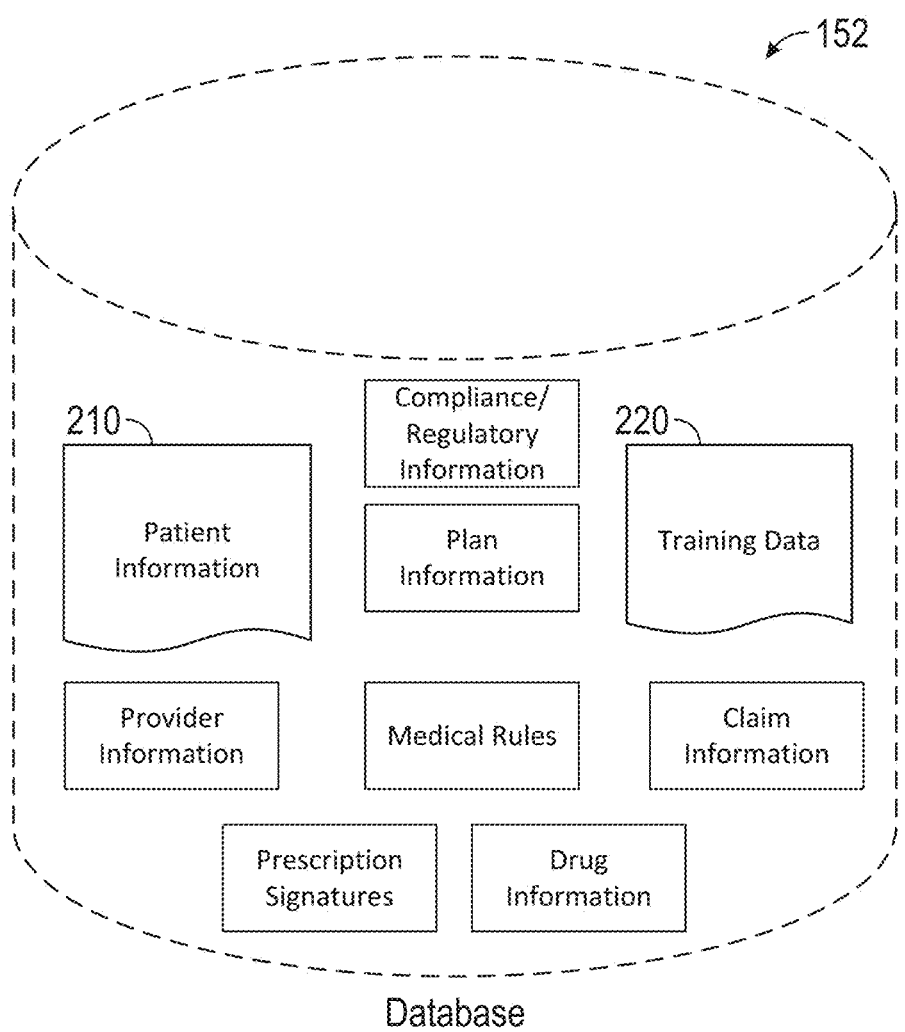
FIG. 2 is an example database that may be deployed within the system of FIG. 1, according to some examples.

FIG. 2 is an example database 152 that may be deployed within the system of FIG. 1, according to some examples. The database 152 includes patient information 210 and training data 220. The patient information 210 can be generated or accessed by the patient management platform 150. For example, the patient management platform 150 can access one or more patient records from one or more sources, including pharmacy claims, benefit information, prescribing physician information, dispensing information (e.g., where and how the patient obtains their current medications), medicinal drug prescriptions, prescription signatures, demographic information, prescription information including dose quantity and interval, and input from a patient received via a user interface presented on the client device 110 and so forth. The patient management platform 150 can collect this information from the patient records and generates a patient features vector that includes this information.

In some examples, the training data 220 includes training sets including collections of textual drug prescriptions associated with sets of ground truth entity labels for different components of the collections of textual drug prescriptions. The training data 220 is used to train the first machine learning model (e.g., the prescription entity model) implemented by patient management platform 150 to generate estimates of one or more entities associated with a prescription.

In some examples, the training data 220 includes training sets including collections of prescription drug entities corresponding to prescriptions received from one or more healthcare professionals associated with a sets of ground truth medical signatures generated by one or more pharmacists for the prescriptions. The training data 220 is used to train the second machine learning model (e.g., the prescription signature model) implemented by patient management platform 150 to generate estimates of medical signatures associated with prescriptions.

In some examples, the patient management platform 150 and/or the healthcare provider devices 120 can be used to generate the training data 220. Specifically, the healthcare provider devices 120 and/or the patient management platform 150 can receive various medical prescriptions that were created by healthcare professionals. The healthcare provider devices 120 and/or the patient management platform 150 can receive labels (manually and/or automatically) for each component of each of the medical prescriptions that indicate the type of entity associated with each component. This labeled data can be used to train the prescription entity model 154. In some examples, the prescription entity model 154 can include name entity recognition (NER) engine, such as a Spacy custom NER model.

FIG. 3 is a block diagram of an example service of patient management platform 150 that may be deployed within the system of FIG. 1, according to some examples. Training input 310 includes model parameters 312 and training data 320 (e.g., training data 220 (FIG. 2)) which may include paired training data sets 322 (e.g., input-output training pairs) and constraints 326. Model parameters 312 stores or provides the parameters or coefficients of corresponding ones of machine learning models. During training, these parameters 312 are adapted based on the input-output training pairs of the training data sets 322. After the parameters 312 are adapted (after training), the parameters are used by trained models 360 to implement the trained machine learning models on a new set of data 370.

Training data 320 includes constraints 326 which may define the constraints of a given patient information features. The paired training data sets 322 may include sets of input-output pairs, such as pairs of a plurality of medicinal drug prescription features and features of entities associated with the medicinal drug prescriptions. The paired training data sets 322 may include sets of input-output pairs, such as pairs of a plurality of prescription entity features and features of medical signatures associated with the prescription entities. Some components of training input 310 may be stored separately at a different off-site facility or facilities than other components.

Machine learning model(s) training 330 trains one or more machine learning techniques based on the sets of input-output pairs of paired training data sets 322. For example, the model training 330 may train the machine learning (ML) model parameters 312 by minimizing a loss function based on one or more ground-truth data.

The ML models can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, a first ML model of the ML models can be applied to a training batch of medicinal drug prescription features to estimate or generate a prediction of entities of the medicinal drug prescription. In some implementations, a derivative of a loss function is computed based on a comparison of the estimated entities of the medicinal drug prescription and the ground truth entities of the medicinal drug prescription and parameters of the first ML model are updated based on the computed derivative of the loss function. The result of minimizing the loss function for multiple sets of training data trains, adapts, or optimizes the model parameters 312 of the corresponding first ML model. In this way, the first ML model is trained to establish a relationship between a plurality of training medicinal drug prescriptions and ground-truth entities of the medicinal drug prescriptions.

A second ML model of the ML models can be applied to a training batch of prescription entity features to estimate or generate a prediction of the medical signature for the medicinal drug prescription. In some implementations, a derivative of a loss function is computed based on a comparison of the estimated medical signature and the ground truth medical signature of the medicinal drug prescription and parameters of the second ML model are updated based on the computed derivative of the loss function. The result of minimizing the loss function for multiple sets of training data trains, adapts, or optimizes the model parameters 312 of the corresponding second ML model. In this way, the second ML model is trained to establish a relationship between a plurality of training prescription entities and ground-truth medical signatures of the medicinal drug prescriptions.

After the machine learning models are trained, new data 370, including one or more medicinal drug prescription features are received and/or derived from a document being accessed by the patient management platform 150. The first trained machine learning model may be applied to the new data 370 to generate results 380 including a prediction of one or more entities. The one or more entities are applied to the second trained machine learning model to generate a prediction of a medical signature. The predicted medical signature can be represented in a GUI, such as in a prompt overlaid on the GUI that depicts the prescription received from the healthcare provider along with a confidence score and indication of whether the medical signature passes validation.

Figure 4:
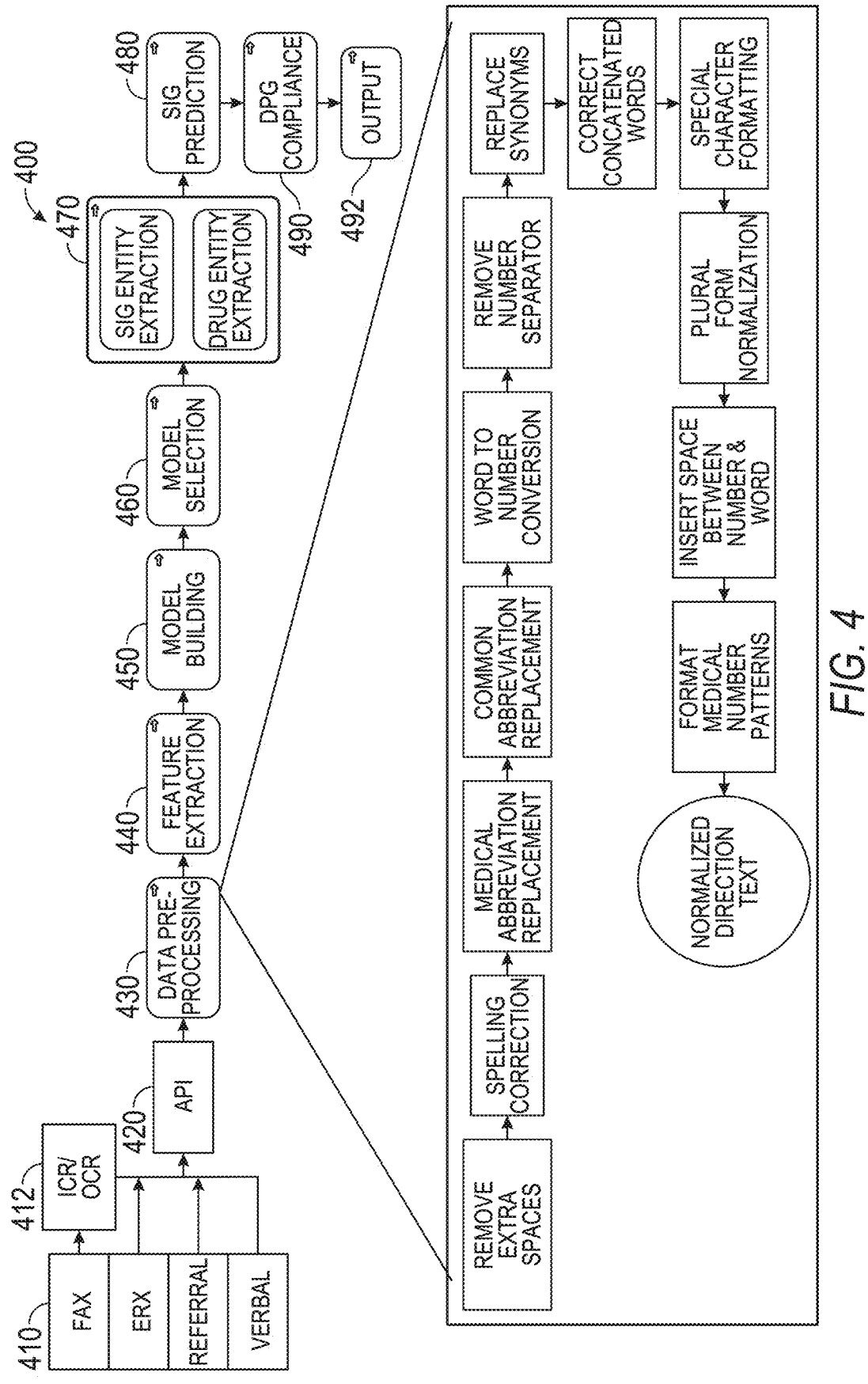
FIG. 4 is a block diagram of an example set of sequences that can be used to generate medical signatures, according to some examples.

FIG. 4 is a block diagram of an example set of sequences that can be used to generate medical signatures, according to some examples. For example, the patient management platform 150 receives a prescription for a drug (e.g., a medicinal drug prescription), via one or more channels 410, by an individual one of the healthcare provider devices 120 of a pharmacist. In some cases, the prescription is received through a fax transmission channel. In such cases, the individual one of the healthcare provider devices 120 of the pharmacist can scan the received fax to generate a document that includes text of the prescription. This document can be uploaded to the patient management platform 150 for further processing. In some cases, the prescription is received through an electronic prescription transmission channel. In such cases, the individual one of the healthcare provider devices 120 of the pharmacist can receive electronically a document that includes text of the prescription which can be automatically uploaded to the patient management platform 150 for further processing. In some cases, the prescription is received through a third-party referral service channel. In such cases, the individual one of the healthcare provider devices 120 of the pharmacist can receive electronically a document that includes text of the prescription which can be automatically uploaded to the patient management platform 150 for further processing. In some cases, the prescription is received through a voice call transmission channel (e.g., through a phone call with the prescribing healthcare professional). In such cases, the individual one of the healthcare provider devices 120 of the pharmacist can draft a document that includes text of the prescription which can then be automatically uploaded to the patient management platform 150 for further processing.

In some examples, the prescription document can be processed by an object character recognition (OCR) engine 412. After the document containing the prescription is processed by the OCR engine 412, metadata can be associated with the document that provides the ASCII characters representing each character of each word in the prescription document. The metadata can be stored in association with the prescription document by the patient management platform 150. The individual one of the healthcare provider devices 120 of the pharmacist can communicate with the patient management platform 150 through one or more application programming interface (API) function calls 420. Namely, the individual one of the healthcare provider devices 120 of the pharmacist can transmit a request via the API function calls 420 that provides as input the prescription document (and optionally the associated metadata) and a request to generate the medical signature for the prescription written by the healthcare professional. For example, the prescription written by the healthcare professional can include the text "BD 1 5 times" which may be converted into the medical signature for a patient to understand which can include the text "take 1 tablet on each day consecutively for 5 days."

In some examples, the patient management platform 150, in response to receiving the function call from the individual one of the healthcare provider devices 120 of the pharmacist, can pre-process the prescription document. For example, the patient management platform 150 can perform one or more data pre-processing operations 430 to re-format and standardize the prescription in the document. In some cases, the one or more data pre-processing operations 430 can include removing extra spaces from the medicinal drug prescription, correcting spelling in the medicinal drug prescription, replacing medical abbreviations in the medicinal drug prescription, replacing common abbreviations in the medicinal drug prescription, formatting a NDC in the medicinal drug prescription, converting words to numbers in the medicinal drug prescription, removing number separators in the medicinal drug prescription, inserting a single space between a number and a word in the medicinal drug prescription, formatting medical number patterns in the medicinal drug prescription, replacing synonyms in the medicinal drug prescription with predetermined words, correcting concatenated words in the medicinal drug prescription, formatting special characters in the medicinal drug prescription, and/or correcting plural forms of words in the medicinal drug prescription. An output of the one or more data pre-processing operations 430 can include normalized or optimized text.

During a training stage, the patient management platform 150 can perform a feature extraction option 440 on the normalized text. The extracted features can be used for performing model building model building 450. The model building 450 can be used to train the prescription entity model 154 and/or the prescription signature model 156 in the manner discussed above. For example, the normalized text features can be processed to manually label or associate individual words/phrases with corresponding entity labels. This labeled data can be used to train the prescription entity model 154. As another example, the normalized text features (and optionally the entity labels) can be associated with a manually written or partially manually written and partially automatically generated medical signature. This medical signature associated with the normalized text features can be used to train the prescription signature model 156.

The patient management platform 150 can process the optimized text provided by the one or more data pre-processing operations 430 to determine whether the text includes a drug identifier and if the optimized text includes MD instructions. If the text includes a drug identifier and lacks an MD instruction, the model selection engine 460 can select from a plurality of entity extraction engines 470, a drug entity extraction model to generate a set of drug entities for the optimized text. If the text includes the MD instruction, the model selection engine 460 can select an entity extraction model to generate a set of entities for the optimized text. The plurality of entity extraction engines 470 can include the prescription entity model 154 and various other entity mapping engines or machine learning models.

Figure 5:
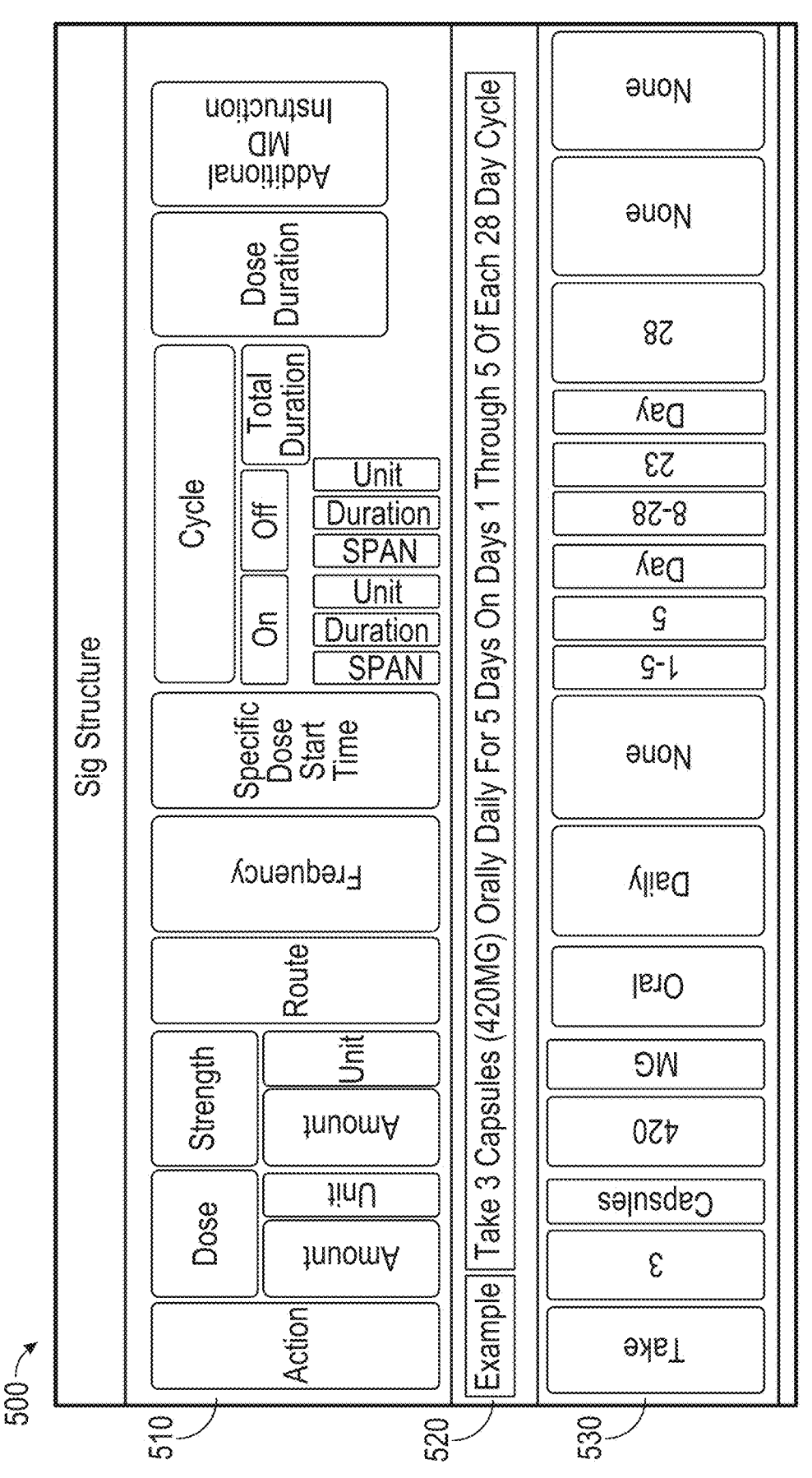
FIG. 5 is an example set of entities extracted from prescriptions, according to some examples.

For example, as shown in FIG. 5, the plurality of entity extraction engines 470 can receive the optimized text from the one or more data pre-processing operations 430 and can map one or more entities according to the signature structure 500. Namely, the plurality of entity extraction engines 470 can map one or more entities 510 to corresponding entity values 530 based on the optimized text. In an example, the action entity of the one or more entities 510 can be populated by the plurality of entity extraction engines 470 to include the value "take" based on the optimized text of the prescription document. The dose entity can be populated with the value "3 capsules" based on the optimized text of the prescription document. The strength entity can be populated with the value "420 mg" based on the optimized text of the prescription document and/or by retrieving dose values from a database that associates drug identifiers with various entity values, such as dose, route, frequency, and so forth. Other entity values can be mapped or populated in a similar manner to generate the entity values 530 shown in FIG. 5.

After the plurality of entity extraction engines 470 complete generating the entity values for the optimized prescription document (text), the patient management platform 150 provides the entity values to the signature prediction engine 480 (which can implement the prescription signature model 156). The signature prediction engine 480 processes the entity values and generates a prediction of the medical signature. For example, the signature prediction engine 480 can generate the predicted medical signature 520 and provide that output in the signature structure 500. The signature prediction engine 480 can generate a score indicating a level of accuracy for the predicted medical signature.

The medical signature predicted by the signature prediction engine 480 can be provided to the DPG compliance engine 490. The DPG compliance engine 490 can apply one or more DPG rules to the predicted medical signature to verify and validate whether the predicted medical signature satisfies the DPG guidelines. The DPG compliance engine 490 can output a score indicating how well the predicted medical signature satisfies the DPG guidelines and/or a binary value indicating whether or not the predicted medical signature passes the DPG guidelines.

The predicted medical signature, the score indicating a level of accuracy for the predicted medical signature, the originally received prescription document, and/or the output of the DPG compliance engine 490 can be simultaneously displayed on a graphical user interface presented as output 492 on the individual one of the healthcare provider devices 120 of the pharmacist. The individual one of the healthcare provider devices 120 of the pharmacist can select an option to accept, revise, or reject the predicted medical signature in the graphical user interface. In response to receiving input from the individual one of the healthcare provider devices 120 of the pharmacist indicating that the pharmacist accepts the predicted medical signature, instructions are transmitted to a dispensing engine. The dispensing engine can generate a label that includes the predicted medical signature and can attach the label to a container of the prescription drugs associated with the predicted medical signature. In response to receiving input from the individual one of the healthcare provider devices 120 of the pharmacist including a modification to the predicted medical signature, training data is updated and used to perform operations for model building 450. Namely, training data is generated that includes the modified predicted medical signature associated with the entity values generated by the plurality of entity extraction engines 470 and associated with the prescription text in the prescription document.

FIG. 6 is a flowchart illustrating example operations and methods of the patient management platform 150 in performing a method or process 600, according to some examples. The process 600 may be embodied in computer-readable instructions for execution by one or more processors such that the operations of the process 600 may be performed in part or in whole by the functional components of the system 100; accordingly, the process 600 is described below by way of example with reference thereto. However, in other embodiments, at least some of the operations of the process 600 may be deployed on various other hardware configurations. Some or all of the operations of process 600 can be in parallel, out of order, or entirely omitted.

At operation 601, the system 100 accesses a communication comprising a medicinal drug prescription associated with a patient, the medical drug prescription being provided in the communication by a healthcare professional, as discussed above.

At operation 602, the system 100 processes, by a first machine learning model, the communication to extract a plurality of entities from the medicinal drug prescription, as discussed above.

At operation 603, the system 100 applies a second machine learning model to the plurality of entities to predict a medical signature, the predicted medical signature comprising directions for the patient to follow to take the medicinal drug, as discussed above.

At operation 604, the system 100 causes a label with the medical signature to be printed and applied to a container that includes the medicinal drug, as discussed above.

Figure 7:
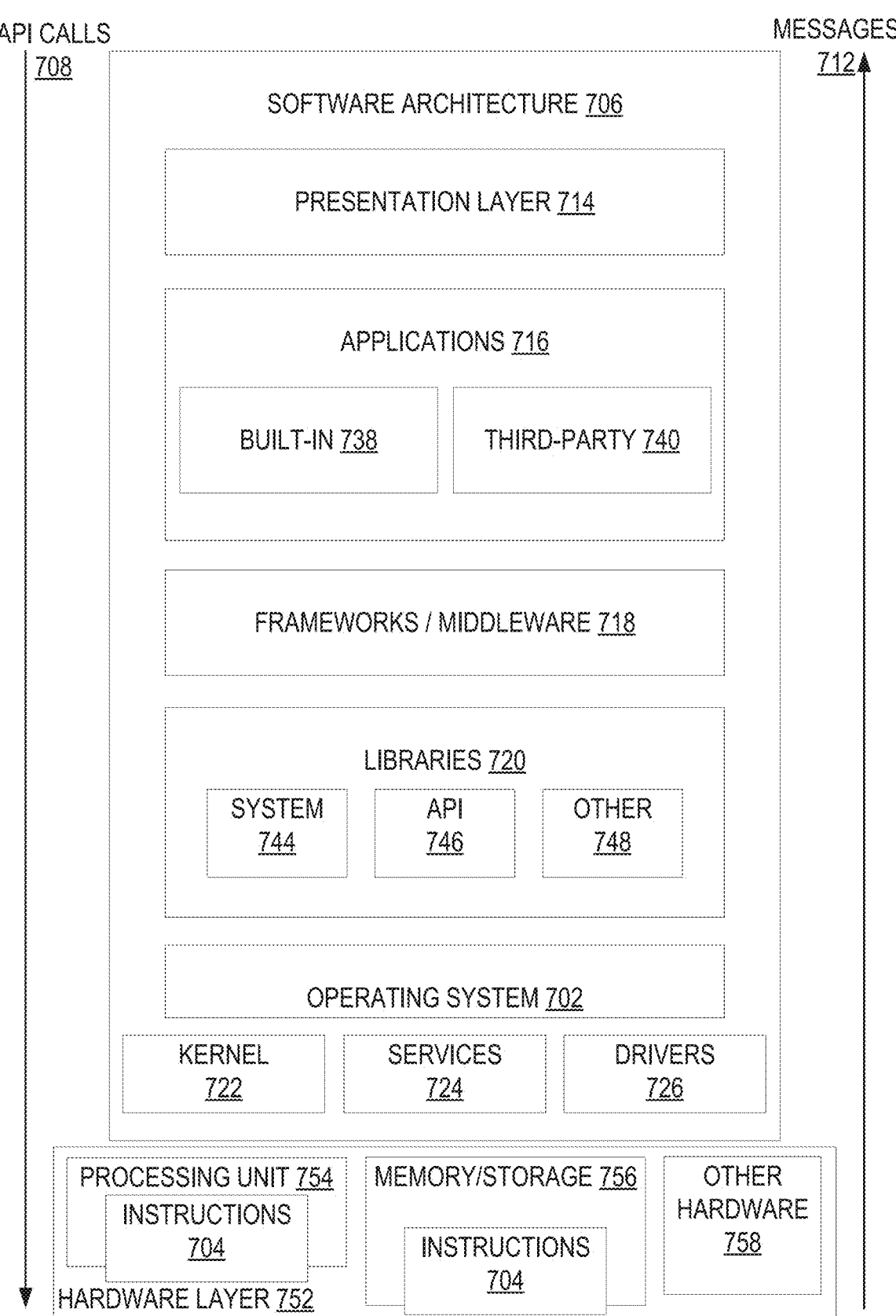
FIG. 7 is a block diagram illustrating an example software architecture, which may be used in conjunction with various hardware architectures herein described.

FIG. 7 is a block diagram illustrating an example software architecture 706, which may be used in conjunction with various hardware architectures herein described. FIG. 7 is a non-limiting example of a software architecture and it will be appreciated that many other architectures may be implemented to facilitate the functionality described herein. The software architecture 706 may execute on hardware such as machine 800 of FIG. 8 that includes, among other things, processors 804, memory 814, and input/output (I/O) components 818. A representative hardware layer 752 is illustrated and can represent, for example, the machine 800 of FIG. 8. The representative hardware layer 752 includes a processing unit 754 having associated executable instructions 704. Executable instructions 704 represent the executable instructions of the software architecture 706, including implementation of the methods, components, and so forth described herein. The hardware layer 752 also includes memory and/or storage devices memory/storage 756, which also have executable instructions 704. The hardware layer 752 may also comprise other hardware 758. The software architecture 706 may be deployed in any one or more of the components shown in FIG. 1. The software architecture 706 can be utilized to apply a machine learning technique or model to generate a prediction of one or more prescription entities and/or medical signatures.

In the example architecture of FIG. 7, the software architecture 706 may be conceptualized as a stack of layers where each layer provides particular functionality. For example, the software architecture 706 may include layers such as an operating system 702, libraries 720, frameworks/middleware 718, applications 716, and a presentation layer 714. Operationally, the applications 716 and/or other components within the layers may invoke API calls 708 through the software stack and receive messages 712 in response to the API calls 708. The layers illustrated are representative in nature and not all software architectures have all layers. For example, some mobile or special purpose operating systems may not provide a frameworks/middleware 718, while others may provide such a layer. Other software architectures may include additional or different layers.

The operating system 702 may manage hardware resources and provide common services. The operating system 702 may include, for example, a kernel 722, services 724, and drivers 726. The kernel 722 may act as an abstraction layer between the hardware and the other software layers. For example, the kernel 722 may be responsible for memory management, processor management (e.g., scheduling), component management, networking, security settings, and so on. The services 724 may provide other common services for the other software layers. The drivers 726 are responsible for controlling or interfacing with the underlying hardware. For instance, the drivers 726 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 720 provide a common infrastructure that is used by the applications 716 and/or other components and/or layers. The libraries 720 provide functionality that allows other software components to perform tasks in an easier fashion than to interface directly with the underlying operating system 702 functionality (e.g., kernel 722, services 724 and/or drivers 726). The libraries 720 may include system libraries 744 (e.g., C standard library) that may provide functions such as memory allocation functions, string manipulation functions, mathematical functions, and the like. In addition, the libraries 720 may include API libraries 746 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 720 may also include a wide variety of other libraries 748 to provide many other APIs to the applications 716 and other software components/devices.

The frameworks/middleware 718 (also sometimes referred to as middleware) provide a higher-level common infrastructure that may be used by the applications 716 and/or other software components/devices. For example, the frameworks/middleware 718 may provide various graphic user interface functions, high-level resource management, high-level location services, and so forth. The frameworks/middleware 718 may provide a broad spectrum of other APIs that may be utilized by the applications 716 and/or other software components/devices, some of which may be specific to a particular operating system 702 or platform.

The applications 716 include built-in applications 738 and/or third-party applications 740. Examples of representative built-in applications 738 may include, but are not limited to, a contacts application, a browser application, a book reader application, a location application, a media application, a messaging application, and/or a game application. Third-party applications 740 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 740 may invoke the API calls 708 provided by the mobile operating system (such as operating system 702) to facilitate functionality described herein.

The applications 716 may use built-in operating system functions (e.g., kernel 722, services 724, and/or drivers 726), libraries 720, and frameworks/middleware 718 to create UIs to interact with users of the system. Alternatively, or additionally, in some systems, interactions with a user may occur through a presentation layer, such as presentation layer 714. In these systems, the application/component "logic" can be separated from the aspects of the application/component that interact with a user.

Figure 8:
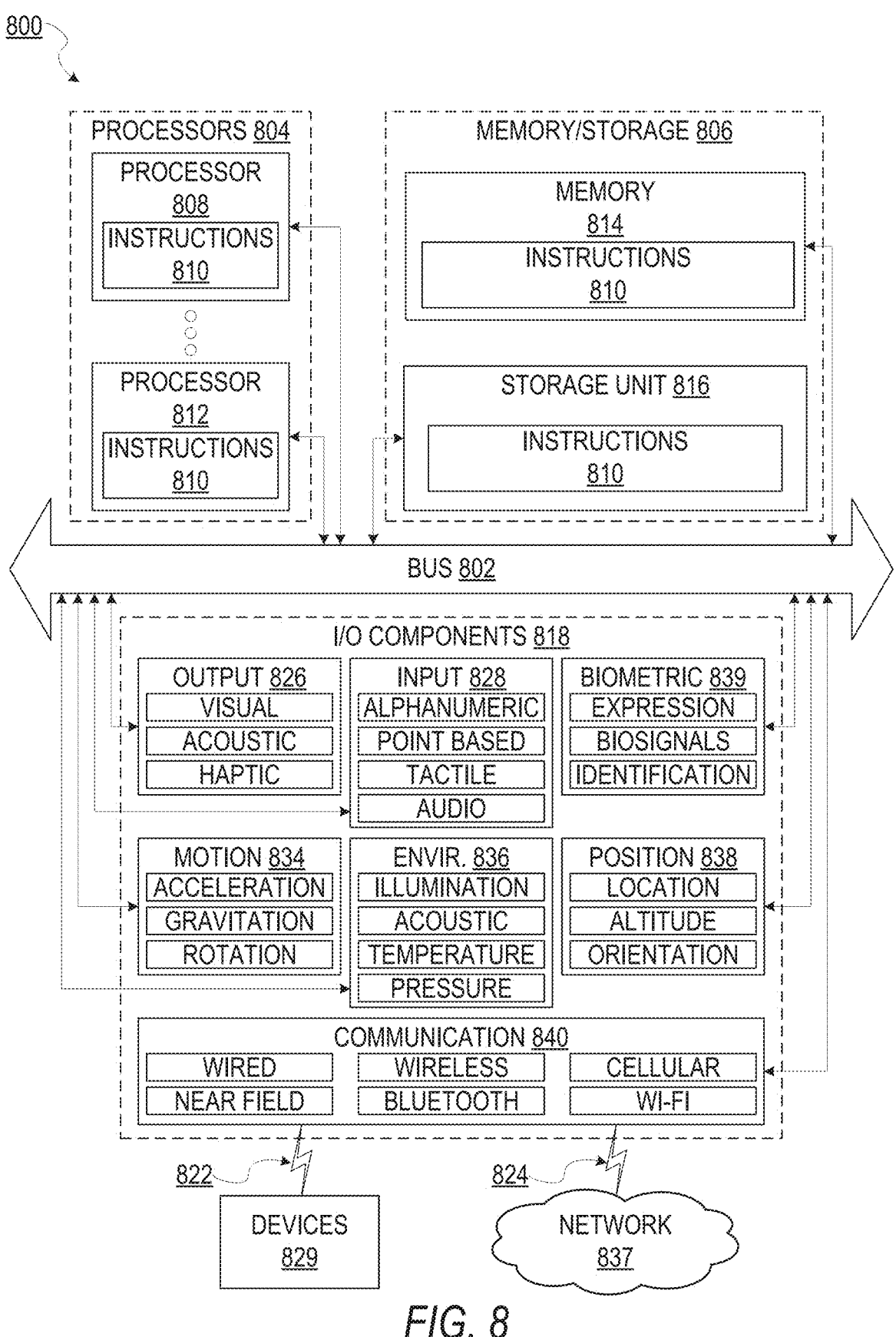
FIG. 8 is a block diagram illustrating components of a machine, according to some examples.

FIG. 8 is a block diagram illustrating components of a machine 800, according to some examples, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 810 (e.g., software, a program, an application, an applet, an app, or other executable code) for causing the machine 800 to perform any one or more of the methodologies discussed herein may be executed. For example, the instructions 810 may be executed by the system 100 to process a medicinal drug prescription document or communication by the patient management platform 150 with trained machine learning models to predict a medical signature for the medicinal drug prescription.

As such, the instructions 810 may be used to implement devices or components described herein. The instructions 810 transform the general, non-programmed machine 800 into a particular machine 800 programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 810, sequentially or otherwise, that specify actions to be taken by machine 800. Further, while only a single machine 800 is illustrated, the term "machine" shall also be taken to include a collection of machines that individually or jointly execute the instructions 810 to perform any one or more of the methodologies discussed herein.

The machine 800 may include processors 804, memory/storage 806, and I/O components 818, which may be configured to communicate with each other such as via a bus 802. In an example embodiment, the processors 804 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 808 and a processor 812 that may execute the instructions 810. The term "processor" is intended to include multi-core processors 804 that may comprise two or more independent processors (sometimes referred to as "cores") that may execute instructions contemporaneously. Although FIG. 8 shows multiple processors 804, the machine 800 may include a single processor with a single core, a single processor with multiple cores (e.g., a multi-core processor), multiple processors with a single core, multiple processors with multiple cores, or any combination thereof.

The memory/storage 806 may include a memory 814, such as a main memory, or other memory storage, database 152, and a storage unit 816, both accessible to the processors 804 such as via the bus 802. The storage unit 816 and memory 814 store the instructions 810 embodying any one or more of the methodologies or functions described herein. The instructions 810 may also reside, completely or partially, within the memory 814, within the storage unit 816, within at least one of the processors 804 (e.g., within the processor's cache memory), or any suitable combination thereof, during execution thereof by the machine 800. Accordingly, the memory 814, the storage unit 816, and the memory of processors 804 are examples of machine-readable media.

The I/O components 818 may include a wide variety of components to receive input, provide output, produce output, transmit information, exchange information, capture measurements, and so on. The specific I/O components 818 that are included in a particular machine 800 will depend on the type of machine. For example, portable machines such as mobile phones will likely include a touch input device or other such input mechanisms, while a headless server machine will likely not include such a touch input device. It will be appreciated that the I/O components 818 may include many other components that are not shown in FIG. 8. The I/O components 818 are grouped according to functionality merely for simplifying the following discussion and the grouping is in no way limiting. In various example embodiments, the I/O components 818 may include output components 826 and input components 828. The output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 828 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further examples, the I/O components 818 may include biometric components 839, motion components 834, environmental components 836, or position components 838 among a wide array of other components. For example, the biometric components 839 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 818 may include communication components 840 operable to couple the machine 800 to a network 837 or devices 829 via coupling 824 and coupling 822, respectively. For example, the communication components 840 may include a network interface component or other suitable device to interface with the network 837. In further examples, communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities.

The devices 829 may be another machine or any of a wide variety of peripheral devices (e.g., a peripheral device coupled via a USB).

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geo-location, location via Wi-Fi® signal triangulation, location via detecting a NFC beacon signal that may indicate a particular location, and so forth.

Figure 9:
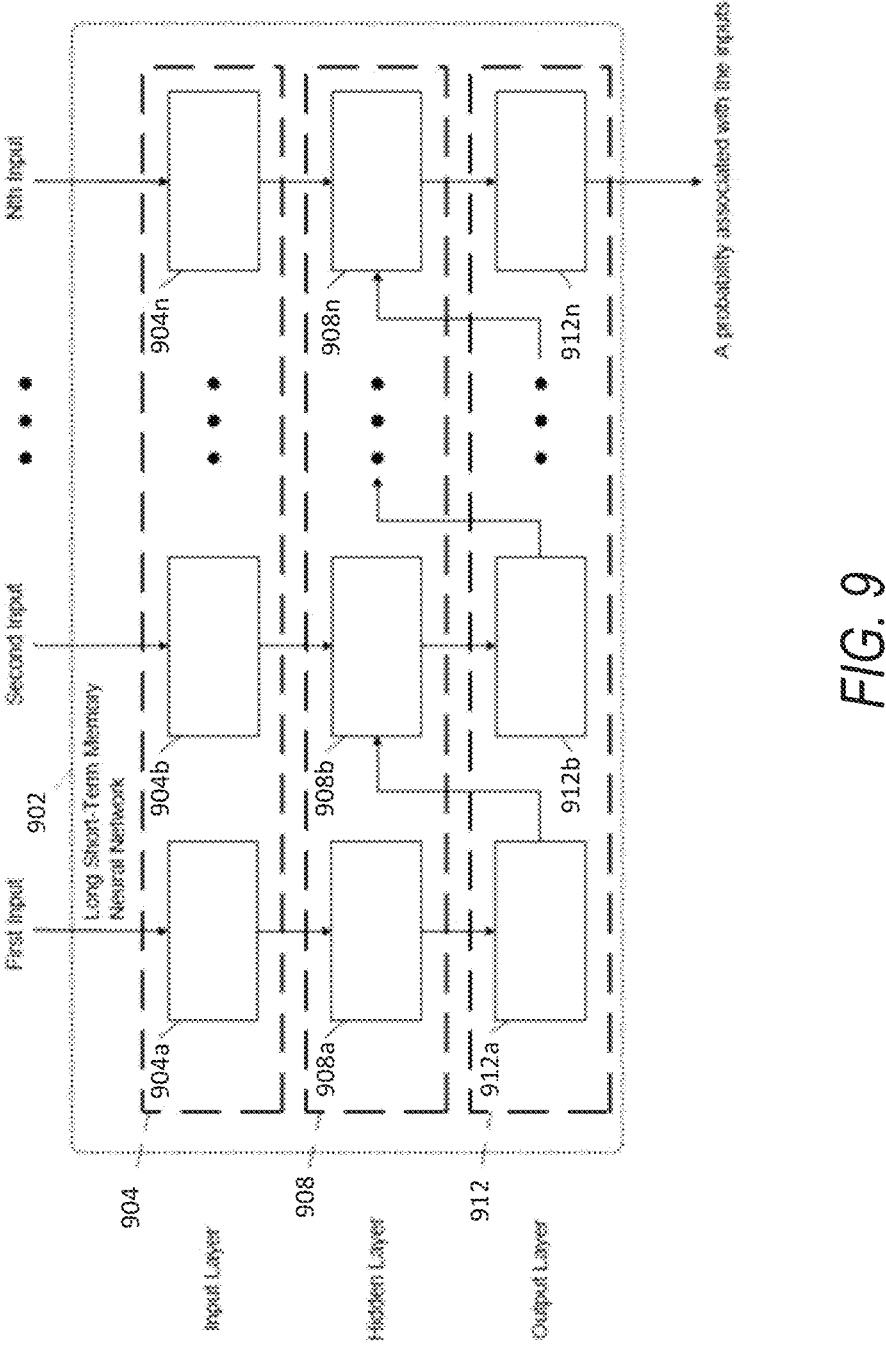
FIG. 9 is a functional block diagram of an example neural network that can be used for the inference engine or other functions (e.g., engines) as described herein to produce a predictive model.

FIG. 9 is a functional block diagram of an example neural network 902 that can be used for the inference engine or other functions (e.g., engines) as described herein to produce a predictive model. The predictive model can identify or generate entities for medicinal drug prescriptions and/or medical signature predictions. In an example, the neural network 902 can be a LSTM neural network. In an example, the neural network 902 can be a recurrent neural network (RNN). The example neural network 902 may be used to implement the machine learning as described herein, and various implementations may use other types of machine learning networks. The neural network 902 includes an input layer 904, a hidden layer 908, and an output layer 912. The input layer 904 includes inputs 904a, 904b . . . 904n. The hidden layer 908 includes neurons 908a, 908b . . . 908n. The output layer 912 includes outputs 912a, 912b . . . 912n.

Each neuron of the hidden layer 908 receives an input from the input layer 904 and outputs a value to the corresponding output in the output layer 912. For example, the neuron 908a receives an input from the input 904a and outputs a value to the output 912a. Each neuron, other than the neuron 908a, also receives an output of a previous neuron as an input. For example, the neuron 908b receives inputs from the input 904b and the output 912a. In this way the output of each neuron is fed forward to the next neuron in the hidden layer 908. The last output 912n in the output layer 912 outputs a probability associated with the inputs 904a-904n. Although the input layer 904, the hidden layer 908, and the output layer 912 are depicted as each including three elements, each layer may contain any number of elements. Neurons can include one or more adjustable parameters, weights, rules, criteria, or the like.

In various implementations, each layer of the neural network 902 must include the same number of elements as each of the other layers of the neural network 902. For example, training features (e.g., collection of textual drug prescriptions associated with a first set of ground truth entity labels for different components of the first collection of textual drug prescriptions and/or prescription drug entities corresponding to prescriptions received from one or more healthcare professionals associated with a first set of ground truth medical signatures generated by one or more pharmacists for the prescriptions) may be processed to create the inputs 904a-904n.

The neural network 902 may implement a first model to produce one or more entity labels for a prescription obtained from a healthcare professional. More specifically, the inputs

904a-904n can include fields of the prescription as data features (binary, vectors, factors or the like) stored in the storage device 110. The features of the prescription can be provided to neurons 908a-908n for analysis and connections between the known facts. The neurons 908a-908n, upon finding connections, provides the potential connections as outputs to the output layer 912, which determines a set of entities associated with the prescription.

The neural network 902 may implement a second model to produce one or more medical signatures associated with prescription entities. More specifically, the inputs 904a-904n can include entities determined by the first model as data features (binary, vectors, factors or the like) stored in the storage device 110. The features of the entities can be provided to neurons 908a-908n for analysis and connections between the known facts. The neurons 908a-908n, upon finding connections, provides the potential connections as outputs to the output layer 912, which determines a medical signature associated with the prescription.

The neural network 902 can perform any of the above calculations. The output of the neural network 902 can be used to trigger display of a prompt that includes the medical signature to an operator in a GUI. For example, the prompt (e.g., notification) can be provided to a PBM, health plan manager, pharmacy, physician, caregiver, and/or a patient. The prompt can include the original prescription received from the healthcare professional, the predicted medical signature, a confidence level associated with the predicted medical signature, an indication of whether the predicted medical signature is compliant according to dispensing practice guidelines (DPG), and/or an option to accept or revise the predicted medical signature. If accepted by selecting the option to accept, the predicted medical signature is sent to a dispensing device to print the predicted medical signature on a label to be attached to a container of the prescription drug.

In some examples, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 904a is connected to each of neurons 908a, 908b . . . 908n.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols. The instructions can carry a selected model that automatically copy text from a first interface and automatically identifies a target location in a second interface at which the copied data from the first interface is suggested to be copied.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra-book, netbook, laptop, multi-processor system, microprocessor-based or programmable consumer electronics, game console, set-top box, or any other communication device that a user may use to access a network. In an example embodiment, the client device is capable of having two or more display that can have two or more interfaces, from which the system selects information to copy and a target location to insert the copied information on two different interfaces. In an example embodiment, the first interface is different than the second interface. The first interface can be produced a different program than the second interface. The first interface can be operating on a different database than the second interface.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes transient signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

Changes and modifications may be made to the disclosed techniques without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method for printing comprising:
   accessing a communication comprising a medicinal drug prescription associated with a patient, the medicinal drug prescription being provided in the communication by a healthcare professional;
   pre-processing the medicinal drug prescription by optimizing text comprising the medicinal drug prescription to generate optimized text;
   processing the optimized text to extract a plurality of entities from the medicinal drug prescription by
      determining if the optimized text includes a drug identifier and lacks a doctor instruction,
      if the optimized text includes the drug identifier and lacks the doctor instruction, selecting from a plurality of entity extraction engines, a drug entity extraction model, generating, with the drug entity extraction model, a set of drug entities for the optimized text, and storing the set of drug entities as the plurality of entities, and
      if the text includes the doctor instruction, selecting a doctor entity extraction model, generating, with the doctor entity extraction model, a set of entities for the optimized text, and storing the set of entities as the plurality of entities,
      wherein the plurality of entity extraction engines includes a first machine learning model;
   applying a second machine learning model to the plurality of entities to predict a medical signature, the predicted medical signature comprising directions for the patient to follow to take the medicinal drug; and
   printing, with a printer, a label with the medical signature to be applied to a container that includes the medicinal drug.

2. The method of claim 1, further comprising:
   generating a confidence score for the predicted medical signature, the confidence score and the predicted medical signature being presented to a pharmacist for evaluation prior to printing the label.

3. The method of claim 2, further comprising:
   determining that the confidence score fails to transgress a threshold; and
   in response to determining that the confidence score fails to transgress the threshold, triggering an alert for a pharmacist to review the predicted medical signature.

4. The method of claim 1, wherein pre-processing the medicinal drug prescription comprises at least one of:
   removing extra spaces from the medicinal drug prescription, correcting spelling in the medicinal drug prescription, replacing medical abbreviations in the medicinal drug prescription, replacing common abbreviations in the medicinal drug prescription, formatting a national drug code (NDC) in the medicinal drug prescription, converting words to numbers in the medicinal drug prescription, removing number separators in the medicinal drug prescription, inserting a single space between a number and a word in the medicinal drug prescription, formatting medical number patterns in the medicinal drug prescription, replacing synonyms in the medicinal drug prescription with predetermined words, correcting concatenated words in the medicinal drug prescription, formatting special characters in the medicinal drug prescription, or correcting plural forms of words in the medicinal drug prescription.

5. The method of claim 1, wherein the medicinal drug prescription is accessed from one of a plurality of channels comprising a fax transmission channel, electronic prescription transmission channel, and voice transmission channel.

6. The method of claim 1, further comprising:

processing the predicted medical signature by a validation engine to determine whether the predicted medical signature is compliant according to dispensing practice guidelines (DPG), the DPG guidelines specifying a manner in which medical signature text is written for different types of prescription drugs.

7. The method of claim 6, further comprising:

presenting, in a graphical user interface on a device associated with a pharmacist, the predicted medical signature in response to determining that the predicted medical signature is compliant, the graphical user interface simultaneously presenting the medicinal drug prescription, received from the healthcare professional and the predicted medical signature.

8. The method of claim 7, wherein the label including the predicted medical signature is generated in response to receiving confirmation via the graphical user interface from the device associated with the pharmacist.

9. The method of claim 1, wherein the first machine learning model comprises a name entity recognition (NER) engine, the NER engine trained to map different words or phrases to corresponding entity types.

10. The method of claim 1, further comprising training the first machine learning model by performing training operations comprising:

obtaining a batch of training data comprising a first collection of textual drug prescriptions associated with a first set of ground truth entity labels for different components of the first collection of textual drug prescriptions;

processing the first collection of textual drug prescriptions by the first machine learning model to generate an estimated set of entity labels;

computing a loss based on a deviation between the estimated set of entity labels and the first set of ground truth entity labels; and updating one or more parameters of the first machine learning model based on the computed loss.

11. The method of claim 1, further comprising training the second machine learning model by performing training operations comprising:

obtaining a batch of training data comprising a first collection of prescription drug entities corresponding to prescriptions received from one or more healthcare professionals associated with a first set of ground truth medical signatures generated by one or more pharmacists for the prescriptions;

processing the first collection of prescription drug entities by the second machine learning model to generate an estimated set of medical signature predictions;

computing a loss based on a deviation between the estimated set of medical signature predictions and the first set of ground truth medical signature predictions; and updating one or more parameters of the second machine learning model based on the computed loss.

12. The method of claim 1, further comprising:

computing similarity between the predicted medical signature and a known set of medical signatures, the similarity comprising a cosine similarity.

13. The method of claim 12, further comprising:

in response to computing the similarity, determining that the predicted medical signature is missing one or more mandatory signature entities; and processing one or more of the known set of medical signatures using statistical probability to predict one or more values for the one or more mandatory signature entities that are missing from the predicted medical signature, the predicted medical signature being revised using the predicted one or more values.

14. The method of claim 1, wherein the plurality of entities comprise one or more of an action, a dose comprising an amount and unit, a strength comprising an amount and unit, a route, a frequency, a dose start time, a cycle comprising unit, duration and span, a dose duration, or additional healthcare professional instruction.

15. The method of claim 1, wherein processing the communication by the first machine learning model comprises:

detecting a drug identifier in the communication; and retrieving, from a database, values for a subset of the plurality of entities associated with the drug identifier.

16. A system for printing, the system comprising:

a memory; and one or more processors coupled to the memory, wherein the memory comprises non-transitory computer instructions that when executed by the one or more processors perform operations comprising:

accessing a communication comprising a medicinal drug prescription associated with a patient, the medicinal drug prescription being provided in the communication by a healthcare professional;

pre-processing the medicinal drug prescription by optimizing text comprising the medicinal drug prescription to generate optimized text;

processing the optimized text to extract a plurality of entities from the medicinal drug prescription by determining if the optimized text includes a drug identifier and lacks a doctor instruction, if the optimized text includes the drug identifier and lacks the doctor instruction, selecting from a plurality of entity extraction engines, a drug entity extraction model, generating, with the drug entity extraction model, a set of drug entities for the optimized text, and storing the set of drug entities as the plurality of entities, and if the text includes the doctor instruction, selecting a doctor entity extraction model, generating, with the doctor entity extraction model, a set of entities for the optimized text, and storing the set of entities as the plurality of entities, wherein the plurality of entity extraction engines includes a first machine learning model;

applying a second machine learning model to the plurality of entities to predict a medical signature, the predicted medical signature comprising directions for the patient to follow to take the medicinal drug; and printing, with a printer, a label with the medical signature to be applied to a container that includes the medicinal drug.

17. The system of claim 16, the operations further comprising:

generating a confidence score for the medical signature, the confidence score and the predicted medical signature being presented to a pharmacist for evaluation prior to printing the label.

18. The system of claim 17, the operations further comprising:

determining that the confidence score fails to transgress a threshold; and in response to determining that the confidence score fails to transgress the threshold, triggering an alert for a pharmacist to review the predicted medical signature.

19. A non-transitory computer readable medium comprising non-transitory computer-readable instructions for performing operations associated with printing, the operations comprising:

accessing a communication comprising a medicinal drug prescription associated with a patient, the medicinal drug prescription being provided in the communication by a healthcare professional;

pre-processing the medicinal drug prescription by optimizing text comprising the medicinal drug prescription to generate optimized text;

processing the optimized text to extract a plurality of entities from the medicinal drug prescription by determining if the optimized text includes a drug identifier and lacks a doctor instruction, if the optimized text includes the drug identifier and lacks the doctor instruction, selecting from a plurality of entity extraction engines, a drug entity extraction model, generating, with the drug entity extraction model, a set of drug entities for the optimized text, and storing the set of drug entities as the plurality of entities, and if the text includes the doctor instruction, selecting a doctor entity extraction model, generating, with the doctor entity extraction model, a set of entities for the optimized text, and storing the set of entities as the plurality of entities, wherein the plurality of entity extraction engines includes a first machine learning model;

applying a second machine learning model to the plurality of entities to predict a medical signature, the predicted medical signature comprising directions for the patient to follow to take the medicinal drug; and printing, with a printer, a label with the medical signature to be printed and applied to a container that includes the medicinal drug.

\* \* \* \* \*